United States Patent
Lui et al.

(10) Patent No.: US 6,706,911 B1
(45) Date of Patent: Mar. 16, 2004

(54) PREPARATION OF 2-HALOACYL-3-AMINOACRYLIC ACID DERIVATIVES

(75) Inventors: Norbert Lui, Köln (DE); Thomas Brackemeyer, Köln (DE); Peter Müller, Odenthal (DE); Marielouise Schneider, Leverkusen (DE)

(73) Assignee: Bayer Aktiengesellschaft, Leverkusen (DE)

( * ) Notice: Subject to any disclaimer, the term of this patent is extended or adjusted under 35 U.S.C. 154(b) by 15 days.

(21) Appl. No.: 10/319,242

(22) Filed: Dec. 13, 2002

(30) Foreign Application Priority Data

Dec. 17, 2001 (DE) .......................................... 101 61 978

(51) Int. Cl.$^7$ ............................................. C07C 69/653
(52) U.S. Cl. ...................................................... 560/219
(58) Field of Search ......................................... 560/219

(56) References Cited

U.S. PATENT DOCUMENTS

| 2,578,788 A | * | 12/1951 | Benneville et al. | ......... 544/171 |
| 5,401,869 A | | 3/1995 | Kraus et al. | ................ 558/375 |
| 6,207,828 B1 | | 3/2001 | Osei-Gyimah et al. | ....... 544/56 |

* cited by examiner

*Primary Examiner*—Alan L. Rotman
*Assistant Examiner*—Golam M M Shameem
(74) *Attorney, Agent, or Firm*—Godfried R. Akorli; Diderico van Eyl

(57) ABSTRACT

The present invention relates to an improved process for preparing 2-haloacyl-3-aminoacrylic acid derivatives and pyrazole-4-carboxylic acids and derivates thereof obtainable from it.

10 Claims, No Drawings

PREPARATION OF 2-HALOACYL-3-AMINOACRYLIC ACID DERIVATIVES

BACKGROUND OF THE INVENTION

1. Field of the Invention

The present invention relates to an improved process for preparing 2-haloacyl-3-aminoacrylic acid derivatives and pyrazole-4-carboxylic acid derivatives obtainable from them.

2. Brief Description of the Prior Art

2-Haloacyl-3-aminoacrylic acid derivatives, for example 2-trifluoroacetyl-3-aminoacrylic esters, are valuable intermediates in preparing substituted pyrazoles which find use as fungicides, pesticides and herbicides.

EP-A 1 000 926 discloses a process for preparing 2-trihaloacetyl-3-amino-acrylic esters by substituting trihaloacetyl acetates using orthoformic acid derivatives. However, the yields of the reaction obtained are only 61.8% and unacceptable for industrial use.

A further method for preparing such compounds is described by Bartnik et al. (Tetrahedron Lett. (1996), 37(48), 8751–8754). β-Chloroacroleins are reacted with secondary amines in diethyl ether at room temperature (RT) in yields of from 44 to 84%.

GHowever, a disadvantage of this process is that the chloroacroleins used as starting compounds are difficult to prepare and accordingly too expensive for industrial use.

There is accordingly a need to develop an improved process for preparing 2-haloacyl-3-aminoacrylic acid derivatives starting from easily obtainable reactants.

SUMMARY OF THE INVENTION

A process for preparing 2-haloacyl-3-aminoacrylic esters has now been found which is characterized in that a) N-substituted 3-aminoacrylic esters are reacted with haloalkylcarboxylic anhydrides in the presence of base and optionally in the presence of solvent.
   If desired, the 2-haloacyl-3-aminoacrylic esters obtained in this manner may be b) converted by reaction with hydrazines to 3-haloalkyl-4-pyrazolecarboxylic esters which c) may be reacted further by acid or alkali hydrolysis to give 3-haloalkyl-4-pyrazolecarboxylic acids.

DETAILED DESCRIPTION OF THE INVENTION

For the purposes of the invention, exemplary and preferred 3-aminoacrylic esters used are of the general formula (I)

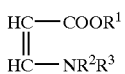

(I)

where
$R^1$ is $C_1$–$C_{12}$-alkyl, $C_6$–$C_{18}$-aryl or $C_7$–$C_{19}$-arylalkyl and
$R^2$ and $R^3$ are each independently $C_1$–$C_{12}$-alkyl or $C_7$–$C_{19}$-arylalkyl.

Preference is given to $R^1$ being $C_1$–$C_4$-alkyl, more preferably methyl or ethyl, and to $R^2$ and $R^3$ each independently being $C_1$–$C_4$-alkyl, more preferably methyl or ethyl.

Particularly preferred 3-aminoacrylic esters of the general formula (I) are methyl 3-(N,N-dimethylamino)acrylate and methyl 3-(N,N-diethylamino)-acrylate, and methyl 3-(N,N-dimethylamino)acrylate is even more preferred.

The 3-aminoacrylic esters to be used can be prepared according to the literature or in a similar manner (EP-A 608 725).

For the purposes of the invention, alkyl is a straight-chain, cyclic, branched or unbranched alkyl radical which may optionally be further substituted by $C_1$–$C_6$-alkoxy radicals, for example methoxy or ethoxy. The same applies to the alkylene moiety of an arylalkyl radical.

For example, $C_1$–$C_4$-alkyl is methyl, ethyl, ethoxyethyl, n-propyl, isopropyl, n-butyl ortert-butyl, $C_1$–$C_8$-alkyl is also n-pentyl, cyclohexyl, n-hexyl, n-octyl or isooctyl, and $C_1$–$C_{12}$-alkyl is also, for example, n-decyl or n-dodecyl.

For the purposes of the invention, alkoxy is a straight-chain, cyclic, branched or unbranched alkoxy radical which may optionally be further substituted by $C_1$–$C_6$-alkoxy radicals, for example methoxy or ethoxy.

For example, $C_1$–$C_6$-alkoxy is methoxy, ethoxy, 2-ethoxyethoxy, n-propoxy, isopropoxy, n-butoxy, tert-butoxy or cyclohexyloxy.

For the purposes of the invention, exemplary and preferred aryl radicals are carbocyclic aromatic radicals having from 6 to 18 skeleton carbon atoms ($C_6$–$C_{18}$-aryl), for example phenyl or naphthyl.

The carbocyclic aromatic radicals may be further substituted by up to five identical or different substituents per cycle, for example those selected from the group of chlorine, fluorine, nitro, cyano, $C_1$–$C_4$-alkyl, for example methyl or ethyl, $C_1$–$C_4$-acyl, for example acetyl, $C_1$–$C_4$-alkoxy, for example methoxy or ethoxy, $C_6$–$C_{12}$-aryl, for example phenyl, $C_7$–$C_{13}$-arylalkyl, for example benzyl, or $C_6$–$C_{12}$-aryloxy, for example phenoxy.

Examples of $C_6$–$C_{10}$-aryl radicals include phenyl, o-, m- and p-tolyl, o-, m- and p-anisyl and naphthyl, and examples of $C_6$–$C_{18}$-aryl also include, for example, anthracenyl.

The same applies to the aryl moiety of an arylalkyl radical. $C_7$–$C_{13}$-Arylalkyl is, for example, benzyl or the isomeric 1-methylbenzyls, and $C_7$–$C_{13}$-arylalkyl is also, for example, fluorenyl.

In step a) of the process according to the invention, haloalkylcarboxylic anhydrides are used.

For the purposes of the invention, haloalkylcarboxylic anhydrides are not only symmetric anhydrides or mixed anhydrides of different haloalkylcarboxylic acids, but also mixed anhydrides of haloalkylcarboxylic acids with organic acids, for example sulphonic acids, or inorganic acids, for example hydrohalic acids. The latter are frequently also termed haloalkylcarbonyl halides.

Exemplary and preferred haloalkylcarboxylic anhydrides are of the general formula (IIa)

(IIa)

where
X is chlorine, bromine or iodine, preferably chlorine and
Hal are each independently chlorine or fluorine, preferably fluorine and
$R^4$ is chlorine, fluorine or $C_1$–$C_{12}$-haloalkyl, $C_1$–$C_{12}$-alkyl, $C_6$–$C_{18}$-aryl or $C_6$–$C_{19}$-arylalkyl, preferably chlorine, fluorine, trifluoromethyl, pentafluoroethyl, nonafluorobutyl or $C_1$–$C_4$-alkyl, more preferably fluorine.

Further exemplary and preferred haloalkylcarboxylic anhydrides are of the general formula (IIb)

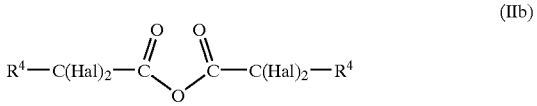

(IIb)

where

Hal and the $R^4$ radicals are each as defined and subject to the same preferences as stated under the general formula (IIa).

Preference is given to the $R^4$ radicals in the general formula (IIb) being identical.

For the purposes of the invention, exemplary and preferred haloalkyl radicals are branched or unbranched, open-chain or cyclic alkyl radicals which may be singly, multiply or fully substituted by halogen atoms selected from the group of chlorine and fluorine.

Exemplary and preferred $C_1$–$C_{12}$-haloalkyl radicals are trifluoromethyl, trichloromethyl, 2,2,2-trifluoroethyl, pentafluoroethyl and nonafluorobutyl.

Exemplary and preferred haloalkylcarboxylic anhydrides are trifluoroacetic anhydride, trifluoroacetyl chloride, trichloroacetic anhydride and trichloroacetyl chloride.

The molar ratio of haloalkylcarboxylic anhydrides to 3-aminoacrylic esters used may be, for example, from 0.3 to 1.5, preferably from 0.8 to 1.1 and more preferably from 0.95 to 1.05.

Exemplary and preferred bases are tertiary nitrogen bases, carbonates and hydrides.

Particular preference is given to using tertiary nitrogen bases, for example tertiary amines, substituted or unsubstituted pyridines and substituted or unsubstituted quinolines.

Very particular preference is given to using pyridine, 2-, 3-, 4-picoline, 2,6-lutidine and quinoline bases, and bases of the general formula (IIIa)

$NR^5R^6R^7$ (IIIa)

where $R^5$, $R^6$ and $R^7$ are each independently $C_1$–$C_{16}$-alkyl, $C_7$–$C_{19}$-arylalkyl or $C_6$–$C_{18}$-aryl, or two radicals together may also form part of a 5- to 8-membered N-heterocyclic radical, or all three radicals together may form part of an N-heterobicyclic or N-heterotricyclic radical having from 5 to 9 ring atoms per cycle which may also contain other heteroatoms, for example oxygen.

Preference is likewise given to using bases of the general formula (IIIb)

$R^8R^9$—N—A—$NR^{10}R^{11}$ (IIIb)

where

A is $C_2$–$C_8$-alkylene, preferably, for example, 1,2-ethylene, 1,3-propylene, 2,3-butylene, 1,2-cyclohexylene or $C_6$–$C_{18}$-arylenes, for example 1,2-phenylene and the $R^8$, $R^9$, $R^{10}$ and $R^{11}$ radicals are each independently $C_1$–$C_{18}$-alkyl, $C_7$–$C_{19}$-arylalkyl or $C_6$–$C_{18}$-aryl or two radicals together may also form part of a 5- to 8-membered N-heterocyclic ring or may form a bridge between the two nitrogen atoms or all four radicals together may form part of a bis-N-heterobicyclic or bis-N-heterotricyclic radical having from 5 to 9 ring atoms per cycle which may also contain heteroatoms, for example oxygen.

Preferred examples of bases of the general formula (IIIa) are trimethylamine, triethylamine, tri-n-propylamine, tri-n-butylamine, tri-n-hexylamine, tricyclohexylamine, N-methylcyclohexylamine, N-ethylcyclohexylamine, N-methylpyrrolidine, N-ethylpyrrolidine, N-methylpiperidine, N-ethylpiperidine, N,N-dimethylaniline, N-methylmorpholine, N-ethylmorpholine, dimethylhexadecylamine and N,N-dimethylbenzylamine.

Equally preferred examples of bases of the general formula (IIIb) are N,N,N,N-tetramethylethylenediamine, N,N-dimethyl-1,4-diazacyclohexane, N,N-diethyl-1,4-diazacyclohexane, 1,8-bis-(dimethylamino)naphthalene, diazabicyclooctane (DABCO), diazabicyclononane (DBN) and diazabicycloundecane (DBU).

Very particular preference is given to using triethylamine as base.

The molar ratio of base to haloalkylcarboxylic anhydrides used may be, for example, from 0.3 to 3, preferably from 1.0 to 2.0 and more preferably from 1.05 to 1.5.

The use of larger quantities of base is not critical but uneconomical.

The reaction of the 3-aminoacrylic esters with haloalkylcarboxylic anhydrides in the presence of base may be carried out at temperatures of, for example, from −30 to 120° C., preferably from −10 to 20° C.

Preference is given to carrying out the reaction in the presence of solvent.

Examples of useful solvents include aliphatic or aromatic hydrocarbons which may further be substituted by fluorine and chlorine atoms, and ethers, for example THF or dioxane.

Exemplary and preferred solvents include toluene, o-, m-, p-xylene, chlorobenzene, fluorobenzene, the isomeric chlorofluorobenzenes, dichloromethane, n-hexane, cyclohexane, methylcyclohexane, heptane, octane, isooctane, petroleum ether, petroleum fractions, THF and dioxane, and particular preference is given to toluene.

The solvent can be used in a quantity of, for example, 50 to 1000 ml of solvent per mole of 3-aminoacrylic acid derivative. This quantity is preferably from 100 to 600 ml. Larger solvent quantities are not critical, but uneconomical.

The process according to the invention may be, for example, to initially charge the base and haloalkylcarboxylic anhydride in a solvent and add the 3-aminoacrylic acid derivative.

In a preferred embodiment of the process according to the invention, the 3-amino-acrylic acid derivative and base are initially charged in a solvent and the haloalkylcarboxylic anhydride is added.

The workup procedure may be, for example, to remove any precipitated salts, for example by filtration, centrifugation or sedimentation and decantation, and to either directly further react the reaction solution obtained in this manner or concentrate it, for example to dryness, to obtain the 2-haloacyl-3-aminoacrylic ester.

The 2-haloacyl-3-aminoacrylic acid derivatives may optionally be further purified by distillation, but this is unnecessary for use for preparing 3-haloalkyl-4-pyrazolecarboxylic esters.

According to the invention, the exemplary and preferred 2-haloacyl-3-aminoacrylic esters obtained are of the general formula (IV)

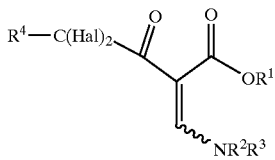
(IV)

where
Hal and $R^4$ are each as defined and subject to the same preferences as stated under the general formula (IIa) and
$R^2$ and $R^3$ radicals are each as defined and subject to the same preferences as stated under the general formula (I).

Preferred compounds of the general formula (IV) include:
methyl 3-N,N-dimethylamino-2-trifluoroacetylacrylate,
ethyl 3-N,N-diethylamino-2-trifluoroacetylacrylate,
methyl 3-N,N-dimethylamino-2-trichloroacetylacrylate,
ethyl 3-N,N-diethylamino-2-trichloroacetylacrylate,
ethyl 3-N,N-dimethylamino-2-trichloroacetylacrylate,
methyl 3-N,N-diethylamino-2-trichloroacetylacrylate,
ethyl 3-N,N-dimethylamino-2-trifluoroacetylacrylate and
ethyl 3-N,N-diethylamino-2-trifluoroacetylacrylate.

The 2-haloacyl-3-aminoacrylic acid derivatives prepared according to the invention are suitable in particular for preparing 3-haloalkyl-4-pyrazolecarboxylic esters (step b).

The 2-haloacyl-3-aminoacrylic esters of the general formula (IV) can exemplarily and preferably be reacted with hydrazines of the general formula (V), optionally in the presence of solvents, to convert them to 3-haloalkyl-4-pyrazolecarboxylic esters of the general formula (VI).

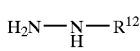
(V)

In the general formula (V), $R^{12}$ is exemplarily and preferably hydrogen, $C_1$–$C_{12}$-alkyl, $C_6$–$C_{18}$-aryl or $C_7$–$C_{19}$-arylalkyl, more preferably $C_1$–$C_4$-alkyl. Very particular preference is given to using hydrazine, methylhydrazine and ethylhydrazine, and methylhydrazine is even more preferred.

In the formula (VI)

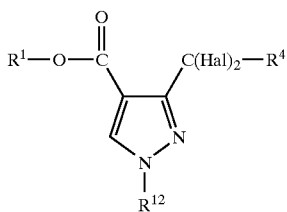
(VI)

$R^1$ is as defined and subject to the same preferences as stated under the general formula (I) and
Hal and $R^4$ are each as defined and subject to the same preferences as stated under the general formula (IIa) and
$R^{12}$ is as defined and subject to the same preferences as stated under the general formula (V).

Preferred compounds of the general formula (VI) include:
methyl 1-methyl-3-trifluoromethyl-4-pyrazolecarboxylate,
ethyl 1-methyl-3-trifluoromethyl-4-pyrazolecarboxylate,
methyl 1-methyl-3-trichloromethyl-4-pyrazolecarboxylate and
ethyl 1-methyl-3-trichloromethyl-4-pyrazolecarboxylate.

Preference is given to carrying out the reaction in the presence of solvent. Exemplary and preferred solvents are those cited above for carrying out step a).

In a particularly preferred embodiment of the process according to the invention, the compounds of the general formula (VI) are prepared using the solution from step a), optionally after removal of solids.

The reaction with hydrazine can exemplarily and preferably be effected at −30 to +80° C., particularly preferred at −20 to 25° C. and most preferably at −10 to 10° C.

The 3-haloalkyl-4-pyrazolecarboxylic acid derivatives may, if desired, be converted in a manner known per se (Houben-Weyl, Methoden der organischen Chemie, $4^{th}$ edition, Volume E5, p 223ff.), for example by acid or alkaline hydrolysis, to 3-haloalkyl-4-pyrazolecarboxylic acids of the general formula (VII)

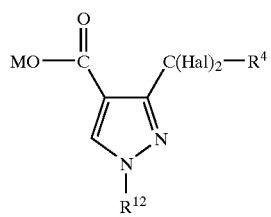
(VII)

where
Hal and $R^4$ are each as defined and subject to the same preferences as stated under the general formula (IIa) and
$R^{12}$ is independently as defined and subject to the same preferences as stated under the general formula (V) and M, in the case of alkaline hydrolysis, is the cation of the base used, or, after acidification or in the case of acid hydrolysis, is hydrogen.

Preference is given to alkaline hydrolysis. This may be affected in a manner known per se, for example by reaction with bases, for example alkali metal hydroxides such as lithium hydroxide, sodium hydroxide or potassium hydroxide, or the aqueous solutions thereof. Examples of useful solvents include water, alcohols, for example methanol, ethanol and isopropanol, aromatic hydrocarbons, for example toluene, acetone or pyridine, or mixtures of such solvents.

In a preferred embodiment of the process according to the invention, the compounds of the general formula (VII) are prepared using the reaction solution from step b).

In a particularly preferred embodiment of the process according to the invention, the compounds of the general formula (VII) are prepared by carrying out steps a), b) and c) without intermediate isolation in the same solvent, preferably aromatic hydrocarbons, for example toluene.

Preferred compounds of the general formula (VII) are:
1-methyl-3-trifluoromethyl-4-pyrazolecarboxylic acid,
3-trifluoromethyl-4-pyrazolecarboxylic acid and
3-trichloromethyl-4-pyrazolecarboxylic acid.

The 2-haloacyl-3-aminoacrylic esters, 2-haloacyl-3-aminoacrylic esters and pyrazole-4-carboxylic acids or salts thereof prepared according to the invention are particularly suitable for the application in a process for preparing pharmaceuticals and agrochemicals, for example fungicides, pesticides and herbicides.

The process according to the invention has the advantage that 2-haloacyl-3-amino-acrylic esters can be prepared from easily obtainable substances in yields of over 95%.

A further advantage of the process according to the invention is that substituted pyrazole-4-carboxylic esters or acids, optionally in the form of their salts, can be obtained without isolating the 2-haloacyl-3-aminoacrylic esters and without changing the solvent.

The invention is further illustrated but is not intended to be limited by the following examples in which all parts and percentages are by weight unless otherwise specified.

EXAMPLES

Example 1

Synthesis of Ethyl 3-N,N-Dimethylamino-2-trifluoroacetylacrylate (Method I)

69 g of ethyl N,N-dimethylaminoacrylate were initially charged in 87 g of toluene and admixed with 101 g of trifluoroacetic anhydride at −15° C. for 1 hour. Stirring was continued at 25° C. for 1 hour, the reaction mixture was then diluted using 87 g of toluene and then 150 g of water were added to the reaction mixture. Stirring was continued for a further 15 minutes and the organic phase which formed was removed. The aqueous phase was extracted using 75 ml of toluene, the organic phases dried over magnesium sulphate and the solvent removed under reduced pressure. 100.01 g of ethyl 3-N,N-dimethylamino-2-trifluoroacetylacrylate were obtained in a purity of 98% (GC). This corresponds to a yield of 85% of theory.

The product may also be used as a solution in toluene with further workup for subsequent syntheses.

Example 2

Synthesis of Ethyl 3-N,N-Dimethylamino-2-trifluoroacetylacrylate (Method II)

128 g of ethyl N,N-dimethylaminoacrylate, 98 g of triethylamine and 312 g of toluene were initially charged and 120 g of trifluoroacetyl chloride were added at 10° C. within 3.5 hours. Stirring was continued at 10° C. for 1 hour, then the reaction mixture was heated to 50° C. and 150 g of water were added. Stirring was continued for a further 15 minutes and the organic phase which formed was removed. The aqueous phase was extracted using toluene and the combined organic phases were used again directly without further workup for the pyrazole formation. 652 g of a toluenic solution having an ethyl 3-N,N-dimethylamino-2-trifluoroacetylacrylate content of 32% (GC-ISTD) were obtained. This corresponds to a yield of 98% of theory.

Example 3

Synthesis of Ethyl 3-N,N-Dimethylamino-2-trifluoroacetylacrylate (Method III)

143 g of ethyl N,N-dimethylaminoacrylate, 111 g of triethylamine and 182 g of toluene were initially charged and 149 g of trifluoroacetyl chloride were added at −10° C. to −5° C. within 3.5 hours. The suspension was then heated to 50° C., the solid isolated and washed with toluene. The combined organic phases were used directly without further workup for subsequent syntheses. 637 g of toluenic solution having an ethyl 3-N,N-dimethylamino-2-trifluoroacetylacrylate content of 37% (GC-ISTD) were obtained. This corresponds to a yield of 98% of theory.

Example 4

Synthesis of Ethyl 1-Methyl-3-trifluoromethyl-4-pyrazolecarboxylate

A solution of 23 g of methylhydrazine dissolved in 87 g of toluene was added dropwise to 300 g of the toluenic solution from Example 2 at 0° C. within 90 minutes. The reaction mixture was then stirred at 0° C. for a further 1 hour. The toluene was distilled off under reduced pressure (<100 mbar) and temperatures of no more than 45° C., and replaced by 100 g of water. To complete the crystallization, the suspension was cooled to 0° C. within 45 minutes and stirred at this temperature for a further 15 minutes, and the solid was isolated on a frit. The crude product was washed with 30 g of n-hexane and dried at RT under reduced pressure.

73 g of ethyl 1-methyl-3-trifluoromethyl-4-pyrazolecarboxylate were obtained. This corresponds to a yield of 82% of theory.

Example 5

1-Methyl-3-trifluoromethyl-4-pyrazolecarboxylic Acid 50 g of ethyl 1-methyl-3-trifluoromethyl-4-pyrazolecarboxylate were initially charged with 177 g of toluene and 54 g of 25% sodium hydroxide solution and heated to reflux for 15 hours. The cloudy reaction mixture was cooled to 50° C. and admixed with 69 g of water. The aqueous phase was adjusted to pH 1–2 at 30° C. by adding 83 g of 15% hydrochloric acid, and the product precipitated out of solution. The suspension was stirred for a further 30 minutes at room temperature and for 30 minutes at 0° C., and the crude product was then isolated and washed 3 times with 60 g each time of cold (<10° C.) water. After drying at room temperature and under reduced pressure, 43 g of 1-methyl-3-trifluoromethyl-4-pyrazolecarboxylic acid were obtained. This corresponds to a yield of 98% of theory.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A process for preparing 2-haloacyl-3-aminoacrylic esters, comprising reacting N-substituted 3-aminoacrylic esters with haloalkylcarboxylic anhydrides in the presence of base.

2. The process according to claim 1, wherein the reaction is carried out further in the presence of a solvent.

3. The process according to claim 1, wherein the 3-aminoacrylic esters are of the general formula (I)

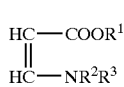

(I)

where

R$^1$ is C$_1$–C$_{12}$-alkyl, C$_6$–C$_{18}$-aryl or C$_7$–C$_{19}$-arylalkyl and R$^2$ and R$^3$ are each independently C$_1$–C$_{12}$-alkyl or C$_7$–C$_{19}$-arylalkyl.

4. The process according to claim 1, wherein the 3-aminoacrylic ester is methyl 3-(N,N-dimethylamino) acrylate.

5. The process according to claim 1, wherein the haloalkylcarboxylic anhydrides are of the general formula (IIa) or (IIb)

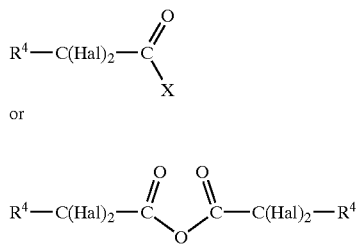

(IIa)

or (IIb)

where

X is chlorine, bromine or iodine and

Hal are each independently chlorine or fluorine and $R^4$ is chlorine, fluorine, $C_1$–$C_{12}$-haloalkyl, $C_1$–$C_{12}$-alkyl, $C_6$–$C_{18}$-aryl or $C_6$–$C_{19}$-arylalkyl.

6. The process according to claim 1, wherein the haloalkylcarboxylic anhydrides are trifluoroacetic anhydride or trifluoroacetyl chloride.

7. The process according to claim 1, wherein the bases are tertiary nitrogen bases.

8. The process according to claim 1, wherein the molar ratio of base to haloalkylcarboxylic anhydrides is from 0.3 to 3.

9. The process according to claim 1, wherein the reaction temperature is from –30 to 120° C.

10. The process according to claim 1, wherein the molar ratio of haloalkylcarboxylic anhydrides to 3-aminoacrylic esters is from 0.3 to 1.5.

* * * * *